(12) United States Patent
Revivo

(10) Patent No.: US 7,101,578 B1
(45) Date of Patent: Sep. 5, 2006

(54) SALT SORBET FACIAL AND BODY SCRUB

(75) Inventor: Jacob Revivo, Sherman Oaks, CA (US)

(73) Assignee: SPA de Soleil, Inc., Sun Valley, CA (US)

( * ) Notice: Subject to any disclaimer, the term of this patent is extended or adjusted under 35 U.S.C. 154(b) by 0 days.

(21) Appl. No.: 10/791,157

(22) Filed: Mar. 1, 2004

(51) Int. Cl.
*A61K 36/286* (2006.01)

(52) U.S. Cl. .................. 424/725; 424/680; 424/401; 514/167; 514/168; 514/458; 514/474

(58) Field of Classification Search ............. 424/725
See application file for complete search history.

(56) References Cited

U.S. PATENT DOCUMENTS

| | | | |
|---|---|---|---|
| 4,776,970 | A | 10/1988 | Hayashi |
| 5,534,265 | A | 7/1996 | Fowler |
| 5,558,855 | A | 9/1996 | Quay |
| 5,595,723 | A | 1/1997 | Quay |
| 5,658,577 | A | 8/1997 | Fowler |
| 5,707,607 | A | 1/1998 | Quay |
| 5,866,145 | A * | 2/1999 | Stavroff et al. ............. 424/401 |
| 5,876,696 | A | 3/1999 | Quay |
| 6,306,805 | B1 | 10/2001 | Bratescu |
| 6,338,855 | B1 | 1/2002 | Albacarys |
| 2002/0012697 | A1 * | 1/2002 | Schwartz ................ 424/450 |
| 2002/0037303 | A1 * | 3/2002 | Deckers et al. ............ 424/401 |

FOREIGN PATENT DOCUMENTS

| | | |
|---|---|---|
| EP | 8711699.2 | 8/1987 |
| EP | 93303880.4 | 5/1993 |
| WO | PCT/US95/10485 | 8/1995 |
| WO | PCT/US99/10405 | 5/1999 |

* cited by examiner

*Primary Examiner*—Susan D. Coe
(74) *Attorney, Agent, or Firm*—Thomas I. Rozsa; Tony D. Chen

(57) ABSTRACT

The present invention is a salt sorbet facial and body scrub which has enhanced properties to deep clean skin, exfoliate dead skin cells in an efficient manner, and at the same time not damage sensitive skin, especially on a woman's face. It is an object of the present invention to provide an improved facial and body scrub which will provide deep cleaning action to cleanse skin pores in an efficient manner and also to exfoliate skin in an efficient manner. It is a further object of the present invention to provide an improved exfoliating facial and body scrub which although effective for cleaning and exfoliating skin, is not so abrasive as to create any damage to sensitive skin areas, especially on a woman's face. It is a further object of the present invention to provide a cost efficient combination of elements and process for creating an improved facial and body scrub.

12 Claims, No Drawings

SALT SORBET FACIAL AND BODY SCRUB

BACKGROUND OF THE INVENTION

1. Field of the Invention

The present invention generally relates to cosmetic cleansing products and in particular, to cosmetics products which are used to both clean and exfoliate dead skin cells from the face and other parts of the body such as the hands, arms, torso, back and legs.

2. Description of the Prior Art

The following prior art references are found to be relevant in the area of the present invention:

1. U.S. Pat. No. 4,776,970 issued to Hayashi on Oct. 11, 1988 for "Lubricant For Use In Parer Coating And Method For Producing The Same" (hereafter the "Hayashi Patent");
2. U.S. Pat. No. 5,534,265 issued to Fowler on Jul. 9, 1996 for "Thickened Nonabrasive Personal Cleansing Compositions" (hereafter the "Fowler Patent");
3. U.S. Pat. No. 5,558,855 issued to Quay on Sep. 24, 1996 for "Phase Shift Colloids As Ultrasound Contrast Agents" (hereafter the "'855 Quay Patent");
4. U.S. Pat. No. 5,595,723 issued to Quay on Jan. 21, 1997 for "Method For Preparing Storage Stable Colloids" (hereafter the "'723 Quay Patent");
5. U.S. Pat. No. 5,658,577 issued to Fowler on Aug. 19, 1997 for "Thickened Nonabrasive Personal Cleansing Compositions" (hereafter the "Fowler Patent");
6. U.S. Pat. No. 5,707,607 issued to Quay on Jan. 13, 1998 for "Phase Shift Colloids As Ultrasound Contrast Agents" (hereafter the "'607 Quay Patent");
7. U.S. Pat. No. 5,876,696 issued to Quay on Mar. 2, 1999 for "Composition Comprising A Fluorine Containing Surfactant And Perfluoropentane For Ultrasound" (hereafter the "'696 Quay Patent");
8. U.S. Pat. No. 6,306,805 B1 issued to Bratescu on Oct. 23, 2001 for "Shampoo And Body Wash Composition Comprising Ternary Surfactant Blends Of Cationic, Anionic, And Bridging Surfactants And methods Of Preparing Same" (hereafter the "Bratescu Patent");
9. U.S. Pat. No. 6,338,855 B1 issued to Albacarys on Jan. 15, 2002 for "Cleansing Articles For Skin And/Or Hair Which Also Deposit Skin Care Actives" (hereafter the "Albacarys Patent");
10. PCT Application No. PCT/US99/10405 filed on May 15, 1999 by Damon Dalrymple for "Clear Personal Care Formulations Containing Quaternary Ammonium Compounds And Other Nitrogen-Containing Compounds" (hereafter the "Dalrymple PCT Application").
11. PCT Application No. PCT/US95/10485 filed on Aug. 15, 1995 by Timothy Fowler for "Personal Cleansing Compositions" (hereafter the "Fowler PCT Application").
12. EPO Application No. 93303880.4 filed on May 19, 1993 by Robert Stanley Lee for "Exfoliant Composition" (hereafter the "Lee European Application").
13. EPO Application No. 87111699.2 filed on Aug. 12, 1987 by Yukio Ozaki for "Scrubbing Agent And Process For Producing The Same" (hereafter the "Ozaki European Application").

The Hayashi Patent discloses a lubricant for use in paper coating and method for producing the same. The purpose of citing the Hayashi Patent is that it discloses a lubricant that contains both sodium polyacrylate and ethylhexyl stearate. However, the purpose and use of this innovation is completely different from the present invention.

The '265 Fowler Patent discloses a non-abrasive thickened aqueous-based personal cleansing composition. The compositions utilize insoluble micronized cleansing particles but do not use ethylhexyl stearate.

The '855 Quay Patent is a phase shift colloidal as ultrasound contrast agent which discloses agents for enhancing the contrast in a diagnostic ultrasound procedure.

The '723 Quay Patent discloses a method for preparing storage stable colloids, again used with ultrasound.

The '607 Quay Patent also discloses a method for preparing storage stable colloids, again used with ultrasound.

The '696 Quay Patent also discloses a method for preparing storage stable colloids, again used with ultrasound.

The '577 Fowler Patent relates to nonabrasive thickened aqueous-based personal cleansing compositions. These compositions utilize insoluble micronized cleansing particles of the fine particle size that are not tactiley perceived by the user during the cleansing process and which provide improved cleansing performance. This patent does not show the use of ethylhexyl stearate.

The Bratescu Patent discloses a shampoo and body wash composition comprising ternary surfactant blends of cationic, anionic, and bridging surfactants and methods of preparing same. This patent does not disclose the use of ethylhexyl stearate.

The Albacarys Patent discloses a substantially dry, disposable, personal cleansing article useful for both cleansing the skin or hair and delivering skin care actives onto the skin or hair. The article comprises a water insoluble substrate, a lathering surfactant, and a skin care active component. This patent does not disclose the use of ethylhexyl stearate.

The PCT Application to Dalrymple discloses a personal care formulation.

The Fowler PCT Application is comparable to the United States case of Fowler.

The Lee European Application discloses an exfoliant composition.

Finally, the Ozaki European Application also discloses a scrubbing agent.

While exfoliating compounds have already been developed in the prior art, many exfoliating compounds either do not provide a sufficiently deep cleansing action or alternatively, may be sufficiently abrasive to damage sensitive skin, especially on a woman's face. Therefore, there is a significant need for an improved facial and body scrub which can deep clean skin tissue and also exfoliate dead skin cells while at the same time not damaging sensitive skin.

SUMMARY OF THE INVENTION

The present invention is a salt sorbet facial and body scrub which has enhanced properties to deep clean skin, exfoliate dead skin cells in an efficient manner, and at the same time not damage sensitive skin, especially on a woman's face.

It is an object of the present invention to provide an improved facial and body scrub which acts as a salt sorbet in that it creates a blown up foam which will provide deep cleaning action to cleanse skin pores in an efficient manner and also to exfoliate skin in an efficient manner.

It is a further object of the present invention to provide a salt sorbet exfoliating facial and body scrub which although effective for cleaning and exfoliating skin, is not so abrasive as to create any damage to sensitive skin areas, especially on a woman's face.

It is a further object of the present invention to provide a cost efficient combination of elements and process for creating an improved facial and body scrub.

Further novel features and other objects of the present invention will become apparent from the following detailed description, discussion and the appended claims, taken in conjunction with the drawings.

DETAILED DESCRIPTION OF THE PREFERRED EMBODIMENTS

Although specific embodiments of the present invention will now be described with reference to the drawings, it should be understood that such embodiments are by way of example only and merely illustrative of but a small number of the many possible specific embodiments which can represent applications of the principles of the present invention. Various changes and modifications obvious to one skilled in the art to which the present invention pertains are deemed to be within the spirit, scope and contemplation of the present invention as further defined in the appended claims.

The present invention comprises the combination of thirteen unique ingredients which contain a combination of ranges of products which will all work to achieve the desired result.

The first preferred combination range of products is set forth in Chart 1 below:

CHART 1

| LIST OF INGREDIENTS | (%) |
| --- | --- |
| 1. Dead Sea Salt (Fine) | 40.00–50.00 |
| 2. *Carthamus Tinctorius* (Safflower) Seed Oil | 28.00–34.00 |
| 3. Dimethicone | 11.50–14.05 |
| 4. Silica | 7.40–9.05 |
| 5. Fragrance | 1.00–3.00 |
| 6. *Persea Gratissima* (Avocado) Oil | 0.14–0.16 |
| 7. *Simmondsia Chinensis* (Jojoba) Oil | 0.14–0.16 |
| 8. Retinyl Palmitate (Vitamin A Palmitate) | 0.05–0.60 |
| 9. Pantothenic Acid (Vitamin B5) | 0.05–0.60 |
| 10. Ascorbic Acid (Vitamin C) | 0.05–0.60 |
| 11. Cholecalciferol (Vitamin D3) | 0.05–0.60 |
| 12. Tocopheryl Acetate (Vitamin E Acetate) | 0.05–0.60 |
| 13. Phytonadione (Vitamin K1) | 0.05–0.60 |

The following fragrances are preferred as the fragrance for the above combination:

1. Apple

2. Blueberry

3. Lemon

4. Raspberry

5. Fresh Peach

An alternative combination range of products is set forth in Chart 2 below:

CHART 2

| LIST OF INGREDIENTS | (%) |
| --- | --- |
| 1. Dead Sea Salt (Fine) | 40.00–50.00 |
| 2. *Carthamus Tinctorius* (Safflower) Seed Oil | 28.00–34.00 |
| 3. Dimethicone | 11.50–14.05 |
| 4. Silica | 7.40–9.05 |
| 5. Fragrance | 1.00–3.00 |
| 6. *Persea Gratissima* (Avocado) Oil | 0.01–0.16 |
| 7. *Simmondsia Chinensis* (Jojoba) Oil | 0.01–0.60 |
| 8. Retinyl Palmitate (Vitamin A Palmitate) | 0.01–0.60 |
| 9. Pantothenic Acid (Vitamin B5) | 0.01–0.60 |
| 10. Ascorbic Acid (Vitamin C) | 0.01–0.60 |
| 11. Cholecalciferol (Vitamin D3) | 0.01–0.60 |
| 12. Tocopheryl Acetate (Vitamin E Acetate) | 0.01–0.60 |
| 13. Phytonadione (Vitamin K1) | 0.01–0.60 |

As with the first preferred combination, the following fragrances are preferred as the fragrance for the above combination:

1. Apple

2. Blueberry

3. Lemon

4. Raspberry

5. Fresh Peach

The appropriate compounding procedure for the preferred ranges of salt sorbet combinations as set forth in both Chart 1 and Chart 2 is as follows:

Compounding Procedure

1. Ensure that all equipment are sanitized before processing.
2. Combine all the oils and vitamins by adding one at a time with constant mixing.
3. Slowly add Silica with constant mixing. Use face mask while dispersing the material to avoid inhalation. Mix until the batch thickens and no solid/lumps present.
4. Add Dimethicone and mix until blended.
5. Add the salt and the fragrance while mixing.

While the preferred combination range of product was set forth in Chart 1, it has been determined through experimentation that the preferred combination percentages of products to achieve the optimum salt sorbet product in accordance with the present invention is set forth in Chart 3 below:

CHART 3

| LIST OF INGREDIENTS | (%) |
| --- | --- |
| 1. *Carthamus Tinctorius* (Safflower) Seed Oil | 31.34 |
| 2. *Persea Gratissima* (Avocado) Oil | 0.15 |
| 3. *Simmondsia Chinensis* (Jojoba) Oil | 0.15 |
| 4. Retinyl Palmitate (Vitamin A Palmitate) | 0.05 |
| 5. Pantothenic Acid (Vitamin B5) | 0.05 |
| 6. Ascorbic Acid (Vitamin C) | 0.05 |
| 7. Cholecalciferol (Vitamin D3) | 0.05 |
| 8. Tocopheryl Acetate (Vitamin E Acetate) | 0.05 |
| 9. Phytonadione (Vitamin K1) | 0.05 |
| 10. Silica | 8.25 |
| 11. Dimethicone | 12.75 |
| 12. Dead Sea Salt | 45.00 |
| 13. Fragrance | 2.00 |

While the alternative combination range product was set forth in Chart 2, it has been determined through experimentation that the preferred combination in the alternative range to achieve the optimum salt sorbet product in accordance with the present invention is set forth in Chart 4 below:

CHART 4

| LIST OF INGREDIENTS | (%) |
| --- | --- |
| 1. *Carthamus Tinctorius* (Safflower) Seed Oil | 30.44 |
| 2. *Persea Gratissima* (Avocado) Oil | 0.10 |
| 3. *Simmondsia Chinensis* (Jojoba) Oil | 0.10 |
| 4. Retinyl Palmitate (Vitamin A Palmitate) | 0.01 |
| 5. Pantothenic Acid (Vitamin B5) | 0.01 |
| 6. Ascorbic Acid (Vitamin C) | 0.01 |
| 7. Cholecalciferol (Vitamin D3) | 0.01 |
| 8. Tocopheryl Acetate (Vitamin E Acetate) | 0.01 |
| 9. Phytonadione (Vitamin K1) | 0.01 |
| 10. Silica | 7.50 |
| 11. Dimethicone | 10.00 |
| 12. Dead Sea Salt | 50.00 |
| 13. Fragrance | 2.00 |

For both detailed combinations as set forth in Charts 3 and 4, the following fragrances are preferred as the fragrance for each detailed combination:

1. Apple
2. Blueberry
3. Lemon
4. Raspberry
5. Fresh Peach

The appropriate compounding procedure for the detailed combination as set forth in both Chart 3 and Chart 4 is as follows:

Preferred Compounding Procedure
1. Ensure that all equipment are cleaned and sanitized before processing.
2. Combine Item #'s 1–9, add one at a time with constant mixing.
3. Slowly add Item # 10, with constant mixing. Use face mask while dispersing the material to avoid inhalation. Mix until the batch thickens and no solid/lumps present.
4. Add Item # 11 and mix until blended.
5. Add the salt and the fragrance while mixing.

After the above items are mixed, the solution is ready for bottling. Through use of the present invention and the unique compounds in combination as set forth above, the present invention creates a vastly improved facial and body scrub with the enhanced properties as discussed above.

Of course the present invention is not intended to be restricted to any particular form or arrangement, or any specific embodiment, or any specific use, disclosed herein, since the same may be modified in various particulars or relations without departing from the spirit or scope of the claimed invention hereinabove shown and described of which the apparatus or method shown is intended only for illustration and for disclosure of an operative embodiment and not to show all of the various forms or modifications in which the present invention might be embodied or operated.

The present invention has been described in considerable detail in order to comply with the patent laws by providing full public disclosure of at least one of its forms. However, such detailed description is not intended in any way to limit the broad features or principles of the present invention, or the scope of the patent to be granted. Therefore, the invention is to be limited only by the scope of the appended claims.

What is claimed is:

1. A salt sorbet facial and body scrub, comprising:
   a. 40.00 percent to 50.00 percent Dead Sea Salt;
   b. 28 percent to 34 percent Carthamus Tinctorius (Safflower) Seed Oil;
   c. 11.50 percent to 14.05 percent Dimethicone;
   d. 7.40 percent to 9.05 percent Silica;
   e. 1.00 percent to 3.00 percent fragrance;
   f. 0.14 percent to 0.16 percent Persea Gratissima (Avocado) Oil;
   g. 0.14 percent to 0.16 percent Simmondsia Chinensis (Jojoba) Oil;
   h. 0.05 percent to 0.60 percent Retinyl Palmitate (Vitamin A Palmitate);
   i. 0.05 percent to 0.6 percent Pantothenic Acid (Vitamin B5);
   j. 0.05 percent to 0.6 percent Ascorbic Acid (Vitamin C);
   k. 0.05 percent to 0.6 percent Cholecalciferol (Vitamin D3);
   l. 0.05 percent to 0.6 percent Tocopheryl Acetate (Vitamin E Acetate);
   m. 0.05 percent to 0.6 percent Phytonadione (Vitamin K); and
   n. the above combination creating a salt sorbet foam which provides a deep cleaning action to cleanse skin pores and exfoliate skin in a manner which will not damage the skin.

2. The salt sorbet facial and body scrub in accordance with claim 1, wherein said fragrance is selected from the group consisting of apple, blueberry, lemon, raspberry and fresh peach.

3. A salt sorbet facial and body scrub, comprising:
   a. 40.00 percent to 50.00 percent Dead Sea Salt;
   b. 28 percent to 34 percent Carthamus Tinctorius (Safflower) Seed Oil;
   c. 11.50 percent to 14.05 percent Dimethicone;
   d. 7.40 percent to 9.05 percent Silica;
   e. 1.00 percent to 3.00 percent fragrance;
   f. 0.01 percent to 0.16 percent Persea Gratissima (Avocado) Oil;
   g. 0.01 percent to 0.60 percent Simmondsia Chinensis (Jojoba) Oil;
   h. 0.01 percent to 0.60 percent Retinyl Palmitate (Vitamin A Palmitate);
   i. 0.01 percent to 0.6 percent Pantothenic Acid (Vitamin B5);
   j. 0.01 percent to 0.6 percent Ascorbic Acid (Vitamin C);
   k. 0.01 percent to 0.6 percent Cholecalciferol (Vitamin D3);
   l. 0.01 percent to 0.6 percent Tocopheryl Acetate (Vitamin E Acetate);
   m. 0.01 percent to 0.6 percent Phytonadione (Vitamin K); and
   n. the above combination creating a salt sorbet foam which provides a deep cleaning action to cleanse skin pores and exfoliate skin in a manner which will not damage the skin.

4. The salt sorbet facial and body scrub in accordance with claim 3, wherein said fragrance is selected from the group consisting of apple, blueberry, lemon, raspberry and fresh peach.

5. A salt sorbet facial and body scrub, comprising:
   a. 31.34 percent Carthamus Tinctorius (Safflower) Seed Oil;
   b. 0.15 percent Persea Gratissima (Avocado) Oil;
   c. 0.15 percent Simmondsia Chinensis (Jojoba) Oil;
   d. 0.05 percent Retinyl Palmitate (Vitamin A Palmitate);
   e. 0.05 percent Pantothenic Acid (Vitamin B5);
   f. 0.05 percent Ascorbic Acid (Vitamin C);
   g. 0.05 percent Cholecalciferol (Vitamin D3);
   h. 0.05 percent Tocopheryl Acetate (Vitamin E Acetate);
   i. 0.05 percent Phytonadione (Vitamin K);
   j. 8.25 percent Silica;
   k. 12.75 percent Dimethicone;
   l. 45 percent Dead Sea Salt;
   m. 2 percent Fragrance; and
   n. the above combination creating a salt sorbet foam which provides a deep cleaning action to cleanse skin pores and exfoliate skin in a manner which will not damage the skin.

6. The salt sorbet facial and body scrub in accordance with claim 5, wherein said fragrance is selected from the group consisting of apple, blueberry, lemon, raspberry and fresh peach.

7. A salt sorbet facial and body scrub, comprising:
   a. 30.44 percent Carthamus Tinctorius (Safflower) Seed Oil;
   b. 0.10 percent Persea Gratissima (Avocado) Oil;

c. 0.10 percent Simmondsia Chinensis (Jojoba) Oil;
d. 0.01 percent Retinyl Palmitate (Vitamin A Palmitate);
e. 0.01 percent Pantothenic Acid (Vitamin B5);
f. 0.01 percent Ascorbic Acid (Vitamin C);
g. 0.01 percent Cholecalciferol (Vitamin D3);
h. 0.01 percent Tocopheryl Acetate (Vitamin E Acetate); and
I. 0.01 percent Phytonadione (Vitamin K);
j. 7.50 percent Silica;
k. 10.00 percent Dimethicone;
l. 50 percent Dead Sea Salt; and
m. 2 percent Fragrance; and
n. the above combination creating a salt sorbet foam which provides a deep cleaning action to cleanse skin pores and exfoliate skin in a manner which will not damage the skin.

8. The salt sorbet facial and body scrub in accordance with claim 7, wherein said fragrance is selected from the group consisting of apple, blueberry, lemon, raspberry and fresh peach.

9. A method of producing a salt sorbet facial and body scrub, comprising:
   a. combining Carthamus Tinctorius (Safflower) Seed Oil, Persea Gratissima (Avocado) Oil, Simmondsia Chinensis (Jojoba) Oil, Retinyl Palmitate (Vitamin A Palmitate), Pantothenic Acid (Vitamin B5), Ascorbic Acid (Vitamin C), Cholecalciferol (Vitamin D3), Tocopheryl Acetate (Vitamin E Acetate) and Phytonadione (Vitamin K) by adding one oil at a time and then one vitamin at a time with constant mixing;
   b. adding Silica with constant mixing;
   c. adding Dimethicone and mixing until blended;
   d. adding Dead Sea Salt while mixing and then adding Fragrance while mixing;
   e. combining the oils, vitamins, Silica, Dimethicone, Dead Sea Salt and Fragrance until the final percentage of all ingredients is in the following ranges: 40.00 percent to 50.00 percent Dead Sea Salt, 28 percent to 34 percent Carthamus Tinctorius (Safflower) Seed Oil, 11.50 percent to 14.05 percent Dimethicone, 7.40 percent to 9.05 percent Silica, 1.00 percent to 3.00 percent fragrance, 0.14 percent to 0.16 percent Persea Gratissima (Avocado) Oil, 0.14 percent to 0.10 percent Simmondsia Chinensis (Jojoba) Oil, 0.05 percent to 0.60 percent Retinyl Palmitate (Vitamin A Palmitate), 0.05 percent to 0.6 percent Pantothenic Acid (Vitamin B5), 0.05 percent to 0.6 percent Ascorbic Acid (Vitamin C), 0.05 percent to 0.6 percent Cholecalciferol (Vitamin D3), 0.05 percent to 0.6 percent Tocopheryl Acetate (Vitamin E Acetate), and 0.05 percent to 0.6 percent Phytonadione (Vitamin K) and
   f. the method creating a salt sorbet foam which provides a deep cleaning action to cleanse skin pores and exfoliate skin in a manner which will not damage the skin.

10. A method of producing a salt sorbet facial and body scrub, comprising:
    a. combining Carthamus Tinctorius (Safflower) Seed Oil, Persea Gratissima (Avocado) Oil, Simmondsia Chinensis (Jojoba) Oil, Retinyl Palmitate (Vitamin A Palmitate), Pantothenic Acid (Vitamin B5), Ascorbic Acid (Vitamin C), Cholecalciferol (Vitamin D3), Tocopheryl Acetate (Vitamin E Acetate) and Phytonadione (Vitamin K) by adding one oil at a time and then one vitamin at a time with constant mixing;
    b. adding Silica with constant mixing;
    c. adding Dimethicone and mixing until blended;
    d. adding Dead Sea Salt while mixing and then adding Fragrance while mixing;
    e. combining the oils, vitamins, Silica, Dimethicone, Dead Sea Salt and Fragrance until the final percentage of all ingredients is in the following ranges: 40.00 percent to 50.00 percent Dead Sea Salt, 28 percent to 34 percent Carthamus Tinctorius (Safflower) Seed Oil, 11.50 percent to 14.05 percent Dimethicone, 7.40 percent to 9.05 percent Silica, 1.00 percent to 3.00 percent fragrance, 0.14 percent to 0.16 percent Persea Gratissima (Avocado) Oil, 0.01 percent to 0.16 percent Simmondsia Chinensis (Jojoba) Oil, 0.01 percent to 0.60 percent Retinyl Palmitate (Vitamin A Palmitate), 0.01 percent to 0.6 percent Pantothenic Acid (Vitamin B5), 0.01 percent to 0.6 percent Ascorbic Acid (Vitamin C), 0.01 percent to 0.6 percent Cholecalciferol (Vitamin D3), 0.01 percent to 0.6 percent Tocopheryl Acetate (Vitamin E Acetate), and 0.01 percent to 0.6 percent Phytonadione (Vitamin K); and
    f. the method creating a salt sorbet foam which provides a deep cleaning action to cleanse skin pores and exfoliate skin in a manner which will not damage the skin.

11. A method of producing a salt sorbet facial and body scrub, comprising:
    a. combining Carthamus Tinctorius (Safflower) Seed Oil, Persea Gratissima (Avocado) Oil, Simmondsia Chinensis (Jojoba) Oil, Retinyl Palmitate (Vitamin A Palmitate), Pantothenic Acid (Vitamin B5), Ascorbic Acid (Vitamin C), Cholecalciferol (Vitamin D3), Tocopheryl Acetate (Vitamin E Acetate) and Phytonadione (Vitamin K) by adding one oil at a time and then one vitamin at a time with constant mixing;
    b. adding Silica with constant mixing;
    c. adding Dimethicone and mixing until blended;
    d. adding Dead Sea Salt while mixing and then adding Fragrance while mixing;
    e. combining the oils, vitamins, Silica, Dimethicone, Dead Sea Salt and Fragrance until the final percentage of all ingredients are in the following percentages: 31.34 percent Carthamus Tinctorius (Safflower) Seed Oil, 0.15 percent Persea Gratissima (Avocado) Oil, 0.15 percent Simmondsia Chinensis (Jojoba) Oil, 0.05 percent Retinyl Palmitate (Vitamin A Palmitate), 0.05 percent Pantothenic Acid (Vitamin B5), 0.05 percent Ascorbic Acid (Vitamin C), 0.05 percent Cholecalciferol (Vitamin D3), 0.05 percent Tocopheryl Acetate (Vitamin E Acetate), 0.05 percent Phytonadione (Vitamin K), 8.25 percent Silica, 12.75 percent Dimethicone, 45 percent Dead Sea Salt, and 2 percent Fragrance; and
    f. the method creating a salt sorbet foam which provides a deep cleaning action to cleanse skin pores and exfoliate skin in a manner which will not damage the skin.

12. A method of producing a salt sorbet facial and body scrub, comprising:
    a. combining Carthamus Tinctorius (Safflower) Seed Oil, Persea Gratissima (Avocado) Oil, Simmondsia Chinensis (Jojoba) Oil, Retinyl Palmitate (Vitamin A Palmitate), Pantothenic Acid (Vitamin B5), Ascorbic Acid (Vitamin C), Cholecalciferol (Vitamin D3), Tocopheryl Acetate (Vitamin E Acetate) and Phytonadione (Vitamin K) by adding one oil at a time and then one vitamin at a time with constant mixing;
    b. adding Silica with constant mixing;
    c. adding Dimethicone and mixing until blended;
    d. adding Dead Sea Salt while mixing and then adding Fragrance while mixing;

e. combining the oils, vitamins, Silica, Dimethicone, Dead Sea Salt and Fragrance until the final percentage of all ingredients are in the following percentages: 30.44 percent Carthamus Tinctorius (Safflower) Seed Oil, 0.10 percent Persea Gratissima (Avocado) Oil, 0.10 percent Simmondsia Chinensis (Jojoba) Oil, 0.01 percent Retinyl Palmitate (Vitamin A Palmitate), 0.01 percent Pantothenic Acid (Vitamin B5); 0.01 percent Ascorbic Acid (Vitamin C), 0.01 percent Cholecalciferol (Vitamin D3); 0.01 percent Tocopheryl Acetate (Vitamin E Acetate), 0.01 percent Phytonadione (Vitamin K), 7.50 percent Silica, 10.00 percent Dimethicone, 50 percent Dead Sea Salt, and 2 percent Fragrance; and f. the method creating a salt sorbet foam which provides a deep cleaning action to cleanse skin pores and exfoliate skin in a manner which will not damage the skin.

* * * * *